United States Patent [19]

Lewis

[11] Patent Number: Plant 7,169

[45] Date of Patent: Feb. 27, 1990

[54] PEACH TREE, "EARLY ELEGANT LADY"

[76] Inventor: Michael D. Lewis, P.O. Box 968, Reedley, Calif. 93654

[21] Appl. No.: 260,070

[22] Filed: Oct. 20, 1988

[51] Int. Cl.[4] ..... A01H 5/00

[52] U.S. Cl. ..... Plt./43

[58] Field of Search ..... Plt./43

[56] References Cited

U.S. PATENT DOCUMENTS

P.P. 4,399 3/1979 Merrill ..... Plt. 43

*Primary Examiner*—James R. Feyrer

*Attorney, Agent, or Firm*—Worrel & Worrel

[57] ABSTRACT

A new and distinct variety of peach tree denominated varietally as "Early Elegant Lady" and which is somewhat similar to the Elegant Lady Peach Tree (U.S. Plant Pat. No. 4,399) with which it is most closely related but which is distinguished therefrom and characterized as to novelty by producing fruit which are mature for commercial harvesting and shipment approximately June 22 through July 1 in Fresno County, Calif., the subject variety maturing for commercial harvesting and shipment approximately seven days earlier than that of the Elegant Lady Peach Tree.

1 Drawing Sheet

BACKGROUND OF THE NEW VARIETY

The present invention relates to a new and distinct variety of Peach Tree denominated varietally as "Early Elegant Lady" and more particularly to such a peach tree which bears a freestone fruit which has a firm, crisp yellow-colored flesh texture at commercial maturity and which is principally characterized as to novelty by a date of ripening of approximately June 22 through July 1 at Reedley, Calif.

Fruit growers have readily recognized for a long period of time that the relative dates that various varieties of peaches become ripe for harvesting is of extreme importance. In particular, it has long been recognized as desirable to provide a peach tree that bears fruit during a portion of the season earlier than other varieties of peach trees, which it most nearly resembles, whereby the fruit produced by such a novel tree can be sent to market at a time when competition is at a minimum and the best price can be negotiated. Further, large scale agriculture has long understood that additional economic benefits can be attained if the harvesting period of a particular orchard is spread over a longer period of time inasmuch as the capitol expenditures required to harvest and transport produce from the orchard can be spread over an extended period of time resulting in an overall lower cost of the final product and increasing the uniformity of production throughout the entire season.

The new and distinct variety of peach tree is characterized as to novelty by producing fruit which are surprisingly similar in their physical characteristics to the Elegant Lady Peach Tree (U.S. Plant Pat. No. 4,399) but which is distinguished therefrom by producing fruit which are mature for harvesting and shipment approximately one week earlier than the Elegant Lady Peach Tree in the San Joaquin Valley of central California.

ORIGIN AND ASEXUAL REPRODUCTION OF THE NEW VARIETY

The inventor has spent a substantial portion of his professional life engaged in farming operations. In this regard, the applicant during routine orchard operations in July of 1986, discovered what appears to be a full tree mutation of the Elegant Lady Peach Tree (U.S. Plant Pat. No. 4,399) within the cultivated area of his commercial orchard located near Avenue 320 and Road 60 in Goshen, Calif. The fruit produced by the full tree mutation was noted at that time to have desirable characteristics. More particularly, it was noted that the mutated tree produced fruit which were mature for harvesting and shipment in advance of the remainder of the trees in the orchard. The inventor marked the mutated tree for subsequent observation. To determine whether the traits of the newly discovered variety were true, the inventor, in January of 1988, removed bud wood from the mutated tree and grafted it into several peach root stocks in the same orchard of origin. The inventor has observed these test trees and the original mutated tree and has evaluated the fruit produced therefrom and it has subsequently been determined that the progeny produced from these test trees have the same identical characteristics as that produced by the original mutated tree.

SUMMARY OF THE NEW VARIETY

The "Early Elegant Lady" Peach Tree hereof is characterized principally as to novelty by bearing fruit which have an attractive skin color and which further are ripe for commercial harvesting and shipment from approximately June 22 through July 1 in Goshen, Calif., the new variety maturing approximately one week earlier than the Elegant Lady Peach Tree at this same location.

BRIEF DESCRIPTION OF THE DRAWINGS

The accompanying drawing is a color photograph of a characteristic twig bearing typical leaves which displays both the dorsal and ventral coloration thereof. Further, the photograph displays several peaches showing their external coloration sufficiently matured for harvesting and shipment; and a peach divided in the axial plane to show the flesh and pit characteristics, all of the subject variety.

DETAILED DESCRIPTION

Referring more specifically to the pomological details of this new and distinct variety of peach tree, the following has been observed under the ecological conditions prevailing in the orchard of the inventor which is located in Goshen, Calif. All major color code designations are by reference to the Dictionary of Color by Maerz and Paul published in 1950, common color names are also used occasionally.

TREE

Size:

*Generally.*—Average.

*Form.*—Upright, with eventual form and density determined by pruning practices.

*Productivity.*—Moderately productive.

*Regularity of bearing.*—Regular, and hardy, when grown under typical San Joaquin Valley climatic conditions.

*Vigor.*—Vigorous.

*Trunk.*—Diameter — Average. Color — Gray-brown, (8-A-9). Lenticels — Numerous large lenticels are present. Raised calloused tissue surrounds the lenticel openings.

*Callous tissue.*—Color — light brown, (7-E-11).

*Branches — size.*—Average.

*Surface texture.*—Medium.

*Branches — color.*—One year old, or older branches display a chocolate brown color, (8-E-10).

*Branches — color.*—Current season growth displays a light green color, (20-G-5), however, exposed shoots are often tinged with red.

*Current season growth.*—Surface texture — Smooth.

LEAVES

Size:

*Generally.*—Large.

*Average length, including petiole.*—Approximately 19.6 cm.

*Average width.*—Approximately 4.7 cm.

Leaf form:

*Generally.*—Lanceolate.

Tip form: Acuminate and at times appearing slightly twisted.

Color:

*Upper leaf surface.*—Dark green, (24-J-8).

*Lower leaf surface.*—Gray-green, (21-C-5).

*Mid-vein.*—The mid-vein on the lower leaf surface appears yellow-green in color (18-I-5).

Mid-vein:

*Thickness.*—Approximately 1.0 mm.

Marginal form:

*Generally.*—Variable, shallowly crenate, at times doubly so. The leaf margin is also slightly undulate.

Leaf petiole:

*Length.*—Considered moderately long, approximately 11 to 13 mm.

*Thickness.*—Approximately 1.5 mm.

*Color.*—Yellow-green (18-J-5). The leaf petiole color is somewhat darker along the petiolar groove.

Leaf glands:

*Form.*—Mixed. In most instances the leaf glands are reniform.

*Numbers.*—One to three reniform glands appear on the base of the leaf margin.

*Shape.*—Globose shaped glands may not always be evident, but are occasionally located on short stalks on the petiole just below the leaf margin.

*Position.*—Alternate.

Stalked glands:

*Generally.*—From zero to three stalked glands may be evident.

*Leaf glands.*—Color — Shiny and light green when young, (18-K-5), however, these colors darken, and the leaf glands deteriorate with advancing maturity.

Leaf stipules:

*Numbers.*—Generally two rather large stipules are evident and are disposed in a position subtending the leaf petiole.

*Average length.*—Approximately 12–14 mm. when fully expanded.

*Marginal edge.*—Serrate, and reddish colored trichomes are located along the marginal edge.

*Color.*—Yellow-green, (18-J-6); further, the stipules are considered to be early deciduous.

FLOWERS

Generally:

*Date of bloom.*—Approximately Feb. 27, 1988 near Goshen, Calif. The date of bloom is considered mid-season in relation to other common peach varieties. Date of full bloom was achieved in 1988 on February 29. The date of bloom is substantially identical to the Elegant Lady Peach Tree, (U.S. Plant Pat. No. 4,399), at the same geographical location.

Size:

*Generally.*—Small.

Flowers:

*Form.*—Non-showy type.

Average diameter: Approximately 23–25 mm. when fully expanded.

Bloom amount:

*Generally.*—Moderate and occasionally light in comparison with the Elegant Lady Peach Tree (U.S. Plant Pat. No. 4,399), at the same geographical location.

Flower bud scales:

*Color.*—Gray-brown, (7-C-9), and pubescent.

Flower buds:

*Size.*—Medium.

*Shape.*—Conic.

Flowers produced per node: Most commonly one flower is produced.

Flower petals:

*Size.*—Small.

*Average length.*—Approximately 12–13 mm.

*Width.*—Approximately 8–10 mm.

Claw:

*Form.*—Short and truncate.

Petals:

*Shape.*—Average in appearance, and strongly cupped in an inward direction.

*Marginal Form.*—Strongly undulate.

*Color.*—Light pink in the central area, (1-D-2), however, a darker pink-rose color appears along the petal margin, (1-H-3). The petal color darkens with senescence.

Pedicel:

*Average length.*—Approximately 3 mm.

*Average thickness.*—Approximately 1 mm.

*Color.*—A shiny green, (20-I-6).

Nectaries:

*Color.*—Orange, (9-J-10). The nectary color darkens with advancing age.

Anthers:

*Size.*—Considered average for the species.

*Color.*—Dorsally the anthers appear light red in color, (3-H-10), however, the anthers have a buff color ventrally, (10-D-4).

Pollen production:

*Generally.*—Abundant.

Pollen color: Yellow, (10-L-3).

Stamens:

*Generally.*—Slightly shorter than the pistil.

*Average length.*—Approximately 13–14 mm.

*Color.*—Light pink, (1-D-1) and occasionally appearing almost white when young; the stamens darken with senescence to a deep rose color, (1-J-4).

Pistil and ovary:

*Generally.*—The pistil is slightly longer than the stamens when fully expanded.

*Size.*—Average.

*Average length.*—Approximately 15 to 16 mm.

*Color.*—Light green, (18-E-2), and pubescent.

FRUIT

Maturity when described: Ripe for commercial harvesting and shipment in 1988, approximately June 22 through July 1 at Goshen, Calif.

Size:

*Generally.*—Uniform and large.

*Average cheek diameter.*—Approximately 76 mm.

*Average suture diameter.*—Approximately 76 mm.

*Average axial diameter.*—Approximately 73 mm.

Form: Uniform and slightly asymmetrical with one side of the fruit appearing slightly larger than the other. Further the fruit is globose in its axial aspect and slightly oblate although occasionally appearing nearly globose in its lateral aspect.

Suture:

*Generally.*—The suture appears as a distinct yet narrow line which extends from the base to the apex. The suture further appears somewhat deeper in the area of the stem basin.

*Color.*—The suture usually takes on the color of the underlying ground or blush color, as opposed to assuming its own distinct coloration. As a general matter, the suture is quite smooth and very little stitching is present. Further, no callous formation is evident.

Ventral surface:

*Shape.*—Rounded and relatively smooth. Further, one side protrudes slightly beyond the other. Moreover, one side usually appears slightly larger than the opposite side.

Stem cavity — size: Average.

Average length: Approximately 34 to 37 mm.

Average width: Approximately 28 to 30 mm.

Average depth: Approximately 14 to 16 mm.

Stem cavity — form: Oval. Further a branch imprint is quite often present in the basal shoulder area.

Base:

*Shape.*—Rounded and appearing slightly truncate. Further, the base of the fruit is usually obliquely disposed with respect to the fruit axis and appears shorter on the ventral suture side.

Apex:

*Shape.*—Rounded and smooth. Further, the pistil point is positioned in a slightly oblique attitude and most often appears slightly depressed. A distinct depression appears on both dorsal and ventral suture sides of the pistil point.

Stem:

*Size.*—Average.

*Average length.*—Approximately 10–13 mm.

*Average width.*—Approximately 3.5 mm.

*Color.*—Light green, (17-J-7).

Skin:

*Thickness.*—Average.

*Flavor.*—Mild.

Tendency to crack: Not observed.

Tenacious to flesh: Yes, at commercial maturity; however, the skin will readily peel away from soft mature fruit.

Pubescence: Present, however, it is short and light.

Skin color:

*Generally.*—The blush color is variable and covers from approximately 50% to 80% of the fruit's surface, depending in some measure on the exposure of the particular fruit to the direct rays of the sun. The blush color is variable, and may appear as a dark garnet red, (7-L-9), to a lighter orange-red, (4-H-11). Further, these same colors may vary somewhat between the stated colors. Moreover the blush color is quite bright and this is in stark contrast to the yellow ground color, (10-K-3). Finally, the skin surface appears very clean and there appears only a few lightly colored dots which may be present over the apical shoulders.

Flesh color at commercial maturity: The flesh color is a uniform yellow which extends from the skin to the pit cavity, (10-J-4).

Pit cavity:

*Color.*—The pit cavity is stained red, (4-J-10), and a few rays of this red coloration extends into the flesh a distance of approximately 6–8 mm. Further, no red flecking is detectable in the flesh.

Flesh texture at commercial maturity: Firm and crisp and becoming melting with advancing maturity.

Flesh fibers:

*Numbers.*—Average.

*Texture.*—Tender, and short.

Ripening: Evenly.

Flavor: Good to excellent; the flavor may be considered slightly acidic.

Aroma: Slight, however pleasant.

Overall eating quality: Considered above average as compared with other peach tree varieties which ripen at approximately the same time of the season.

STONE

Attachment: The subject variety is considered freestone by nature. Further, almost no air space is present in the stone cavity at commercial maturity. The stone will cleanly break free from the flesh with only a few short fibers remaining attached to the stone.

Size: Small to medium.

Average length: Approximately 35–38 mm.

Average width: Approximately 25–27 mm.

Average thickness: Approximately 20–21 mm.

Fibers:

*Numbers.*—Few.

*Length.*—Considered moderately short.

Form:

*Generally.*—Considered irregularly oval and may appear slightly obovate.

Base:

*Shape.*—Rounded. The base angle is oblique to the stone axis and appears shorter on the ventral suture side.

Hilum:

*Size.*—Moderately large.

*Shape.*—Oval and appearing substantially eroded.

Apex:

*Shape.*—Acute and having a short dentate tip.

Stone sides:

*Surface texture.*—Very rough. Further, deep jagged ridges are evident over the apical shoulders and deep irregular pits appear over the lateral surfaces and basally. Moreover the stone sides are nearly equal and may occasionally appear slightly unequal.

Ventral edge:

*Generally.*—Moderately broad from the base to the apex. Low wings converge apically over the apical shoulders and is somewhat eroded basally.

Dorsal edge:

*Texture.*—Moderately rough and having a wide groove basally which extends to a position above mid-stone. Further the apical shoulder portion of the dorsal edge appears substantially eroded and is concavely shaped. The dorsal edge ridges are quite high and prominent, especially near mid-stone.

Stone color:

*Dry.*—Brown. (14-F-9). A moderate amount of light purple staining is evident.

Tendency to split: Not observed.

Fruit use: Fresh market dessert type peach for use in local and long distance shipping.

Keeping quality: Good.

Resistance to disease: No particular susceptibilities were noted.

Although the new variety of peach tree possesses the described characteristics as a result of the growing conditions prevailing in the San Joaquin Valley of central California, it is to be understood that variations of the usual magnitude and characteristics incident to growing conditions, fertilization, pruning and pest control are to be expected.

Having thus described and illustrated my new variety of peach tree, what I claim is:

1. A new and distinct variety of peach tree to be denominated varietally as Early Elegant Lady substantially as illustrated and described and which is characterized principally as to novelty by its production of fruit which are somewhat similar in their overall appearance to the fruit produced by the Elegant Lady Peach Tree (U.S. Plant Pat. No. 4,399) from which it was believed derived as a mutation, but which is distinguished therefrom and characterized principally as to novelty by producing fruit which are ripe for commercial harvesting and shipment approximately seven days earlier than the fruit produced by the Elegant Lady Peach Tree.

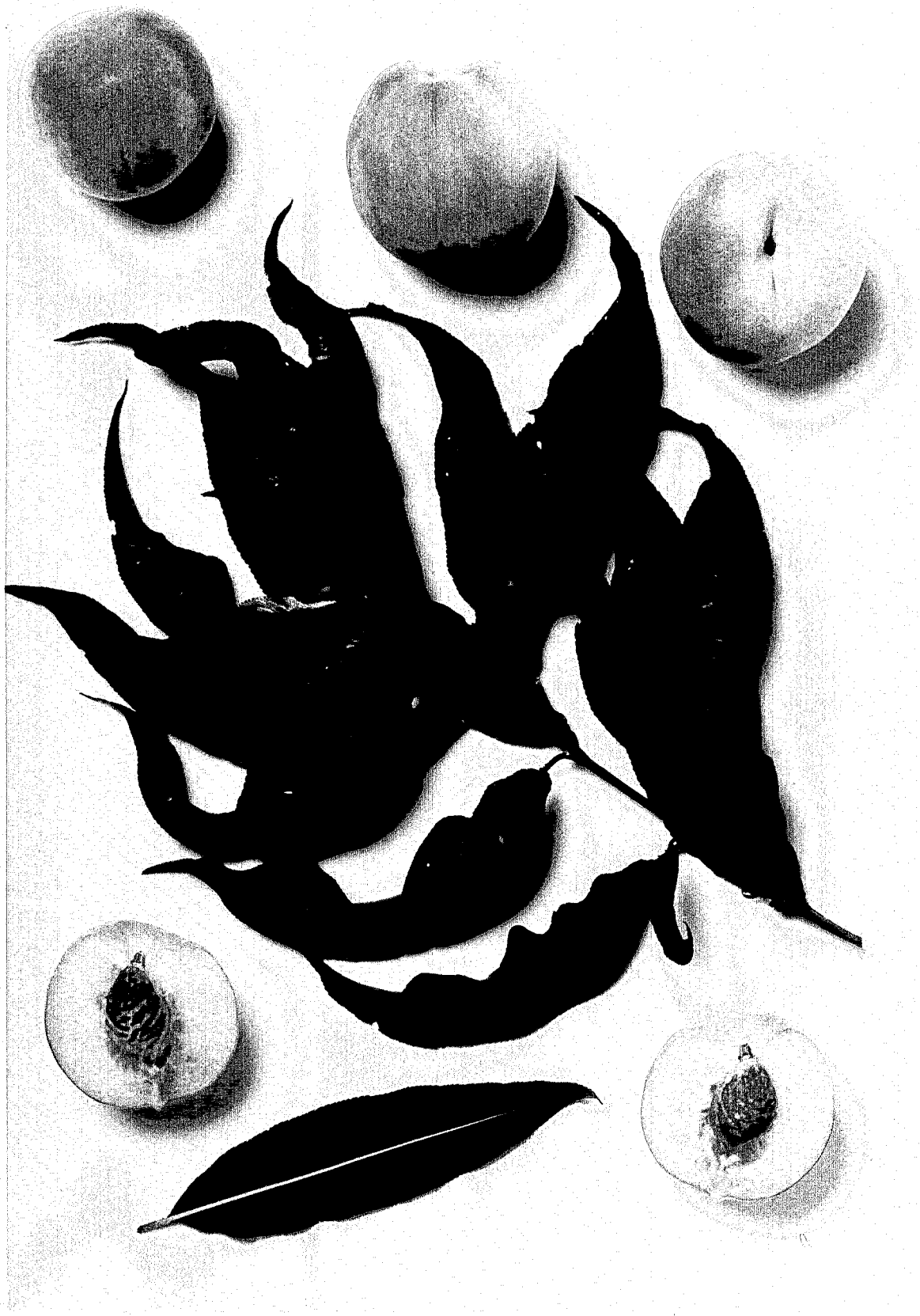

* * * * *